United States Patent
Johnson et al.

(10) Patent No.: US 6,330,827 B1
(45) Date of Patent: Dec. 18, 2001

(54) RESONANT NONLINEAR ULTRASOUND SPECTROSCOPY

(75) Inventors: Paul A. Johnson, Santa Fe; James A. TenCate, Los Alamos, both of NM (US); Robert A. Guyer, Amherst, MA (US); Koen E. A. Van Den Abeele, Sint-Niklaas (BE)

(73) Assignee: The Regents of the University of California, Los Alamos, NM (US)

( * ) Notice: Subject to any disclaimer, the term of this patent is extended or adjusted under 35 U.S.C. 154(b) by 0 days.

(21) Appl. No.: 09/444,219

(22) Filed: Nov. 19, 1999

Related U.S. Application Data
(60) Provisional application No. 60/110,961, filed on Dec. 4, 1998.

(51) Int. Cl.$^7$ ................................................. G01H 13/00
(52) U.S. Cl. ............................................. 73/579; 73/602
(58) Field of Search .................... 73/579, 646, 12.01, 73/598, 602, 760

(56) References Cited

U.S. PATENT DOCUMENTS

| | | | |
|---|---|---|---|
| 4,062,227 | * 12/1977 | Heyman | 73/630 |
| 5,062,296 | * 11/1991 | Migliori | 73/579 |
| 5,146,289 | 9/1992 | Newman | 356/35.5 |
| 5,355,731 | * 10/1994 | Dixon et al. | 73/579 |
| 5,408,880 | * 4/1995 | Rhodes et al. | 73/579 |
| 5,425,272 | * 6/1995 | Rhodes et al. | 73/579 |
| 5,612,495 | 3/1997 | Shimada et al. | 73/579 |
| 5,631,423 | 5/1997 | Rhodes | 73/579 |
| 5,767,415 | 6/1998 | Azbel | 73/847 |
| 5,837,896 | * 11/1998 | Rhodes et al. | 73/579 |
| 5,974,881 | 11/1999 | Donskoy et al. | 73/579 |
| 5,992,234 | * 11/1999 | Rhodes et la. | 73/579 |

OTHER PUBLICATIONS

K.E–A Van Den Abeele et al., "Single Mode Nonlinear Resonance Acoustic Spectroscopy for Damage Detection in Quasi–brittle Materials," Proceedings of the $2^{nd}$ Internation Conference on Emerging Technologies in NDT, Athens, May 24–26, 1999.

P.A. Johnson et al., "Manifestation of Nonlinear Elasticity in Rock: Convincing Evidence Over Large Frequency and Strain Intervals From Laboratory Studies," Nonlinear Processes in Geophysics, 3, pp. 77–88, 1996.

Paul A. Johnson et al., "Resonance and Elastic Nonlinear Phenomena in Rock," Journal of Geophysical Research, vol. 101, No. B5, pp. 11, 553–11, 564, May 10, 1996.

Bernard Zinszner et al., "Influence of Change in Physical State on Elastic Nonlinear Response in Rock: Significance of Effective Pressure and Water Saturation," Journal of Geophysical Research, vol. 102, No. B4, pp. 8105–8120, Apr. 10, 1997.

* cited by examiner

*Primary Examiner*—Hezron Williams
*Assistant Examiner*—Jacques Saint-Surin
(74) *Attorney, Agent, or Firm*—Ray G. Wilson

(57) ABSTRACT

Components with defects are identified from the response to strains applied at acoustic and ultrasound frequencies. The relative resonance frequency shift $|\Delta f/f_0|$, is determined as a function of applied strain amplitude for an acceptable component, where $f_0$ is the frequency of the resonance peak at the lowest amplitude of applied strain and $\Delta f$ is the frequency shift of the resonance peak of a selected mode to determine a reference relationship. Then, the relative resonance frequency shift $|\Delta f/f_0|$ is determined as a function of applied strain for a component under test, where fo $f_0$ the frequency of the resonance peak at the lowest amplitude of applied strain and $\Delta f$ is the frequency shift of the resonance peak to determine a quality test relationship. The reference relationship is compared with the quality test relationship to determine the presence of defects in the component under test.

2 Claims, 5 Drawing Sheets

RESONANT NONLINEAR ULTRASOUND SPECTROSCOPY

RELATED APPLICATIONS

This application claims the benefit of U.S. provisional application 60/110,961, filed Dec. 4, 1998.

STATEMENT REGARDING FEDERAL RIGHTS

This invention was made with government support under Contract No. W-7405-ENG-36 awarded by the U.S. Department of Energy. The government has certain rights in the invention.

FIELD OF THE INVENTION

The present invention relates generally to resonant ultrasound spectroscopy, and, more particularly for the characterization of material using nonlinear resonant ultrasound spectroscopy.

BACKGROUND OF THE INVENTION

Both Resonant Ultrasound Spectroscopy (RUS) and the pulse echo method for sonic testing of materials rely on the linear elastic properties of the medium for sonic interrogation of damage. RUS relies on observing resonant peak mode splitting for damage diagnostics. The pulse-echo method relies on monitoring reflected sound energy from a damaged region or crack, or from changes in the sound wave speed, and/or wave dissipation of waves that pass through the damaged region.

The pulse-echo method tends to be the least sensitive of these methods for damage diagnostics because, if the impedance contrast (impedance is defined as the wave speed times the material density) between the undamaged and damaged region is not strong, which is often the case, there will be no, or little, reflected energy from that region. Wave speed and/or dissipation of waves passing through a damaged region can be difficult to observe and interpret.

Further, pulse-echo requires one to know where the damage is in advance, because the acoustic source must be directly aimed at the region of damage in order for a result to be obtained. RUS and nonlinear RUS (NRUS) require only one source/receiver position, relying on coupling into all or the most important resonant modes of the sample. This means that knowledge of the damage location is less important. In application of RUS, the mode or modes that are affected by the damage will show a split resonance peak.

RUS has been demonstrated to be significantly more sensitive to damage than the pulse echo method, because RUS takes advantage of small signal attenuation during resonance. In short, RUS is a volumetric measurement rather than a point measurement, and is generally easier to interpret. The primary drawback of RUS is that objects with complicated geometry are very difficult to measure. Pulse echo methods can have the advantage in this situation.

It has been demonstrated that the nonlinear response of materials is far more sensitive to damage than the linear response. Therefore, if damage is present, NRUS can "see" the damage in a more sensitive manner than any linear method, and can monitor progression of damage in a manner that no linear acoustical method can. Even very small damage features can be observed, which is not the case of the pulse echo method, and is only sometimes possible with RUS. The primary drawback is that, like RUS, objects with complicated geometry are very difficult to measure. However, the method works very well if the geometry is simple.

Because of their low aspect ratio "compliant features", i.e., grain contacts, dislocations, cracks, and other thin voids that comprise their microstructure, volumetrically damaged materials, such as rocks or solid materials, metals, and the like, compress more readily that their component solid materials. Further, their elastic moduli vary in response to dynamic wave strain fields passing through them. At strains as low as $10^{-8}$, here is a softening nonlinearity (decrease in modulus) as strain amplitude is increased. This quality produces a rich variety of nonlinear elastic phenomena seen in dynamic experiments and described in several models of nonlinear acoustics: (1) harmonic frequency generation from single frequency waves resonant and propagating; (2) sum and difference frequency generation when more than one frequency is present; (3) hysteresis and end-point memory in stress-strain behavior; (4) resonance peak shifts and peak asymmetry in bar resonance; and (5) slow dynamic elastic behavior. For instance, a symmetrical resonance curve obtained at low strain levels can be highly asymmetric at high strain levels. At the same time, the peak resonance frequency can be shifted downward and waveforms collected near the resonance peak are distorted due to the creation of harmonics.

These complex characteristics of materials having such compliant features have been widely studied in the laboratory. But none of them has been identified as suitable for providing a damage assessment of the material or to provide criteria for accepting or rejecting a component or structure. In accordance with the present invention, a sensitive measure of damage is provided by the frequency shift of the resonant response at increasing strain levels.

Various objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

In accordance with the purposes of the present invention, as embodied and broadly described herein, the present invention includes a method for identifying components with defects using strains applied at acoustical and ultrasound frequencies. The relative resonance frequency shift $|\Delta f/f_0|$ is determined as a function of applied strain for an acceptable component, where $f_0$ is the frequency of the resonance peak at the lowest amplitude of applied strain and $\Delta f$ is the frequency shift of the resonance peak as strain amplitude is increased to determine a reference relationship. Then, the relative resonance frequency shift $|\Delta f/f_0|$ is determined as a function of applied strain for a component under test, where $f_0$ is the frequency of the resonance peak at the lowest amplitude of applied strain and $\Delta f$ is the frequency shift of the resonance peak to determine a quality test relationship. The reference relationship is compared with the quality test relationship to determine the presence of defects in the component under test.

BRIEF DESCRIPTION OF THE DRAWINGS

The accompanying drawings, which are incorporated in and form a part of the specification, illustrate embodiments of the present invention and, together with the description, serve to explain the principles of the invention. In the drawings.

DETAILED DESCRIPTION

Figure 1:
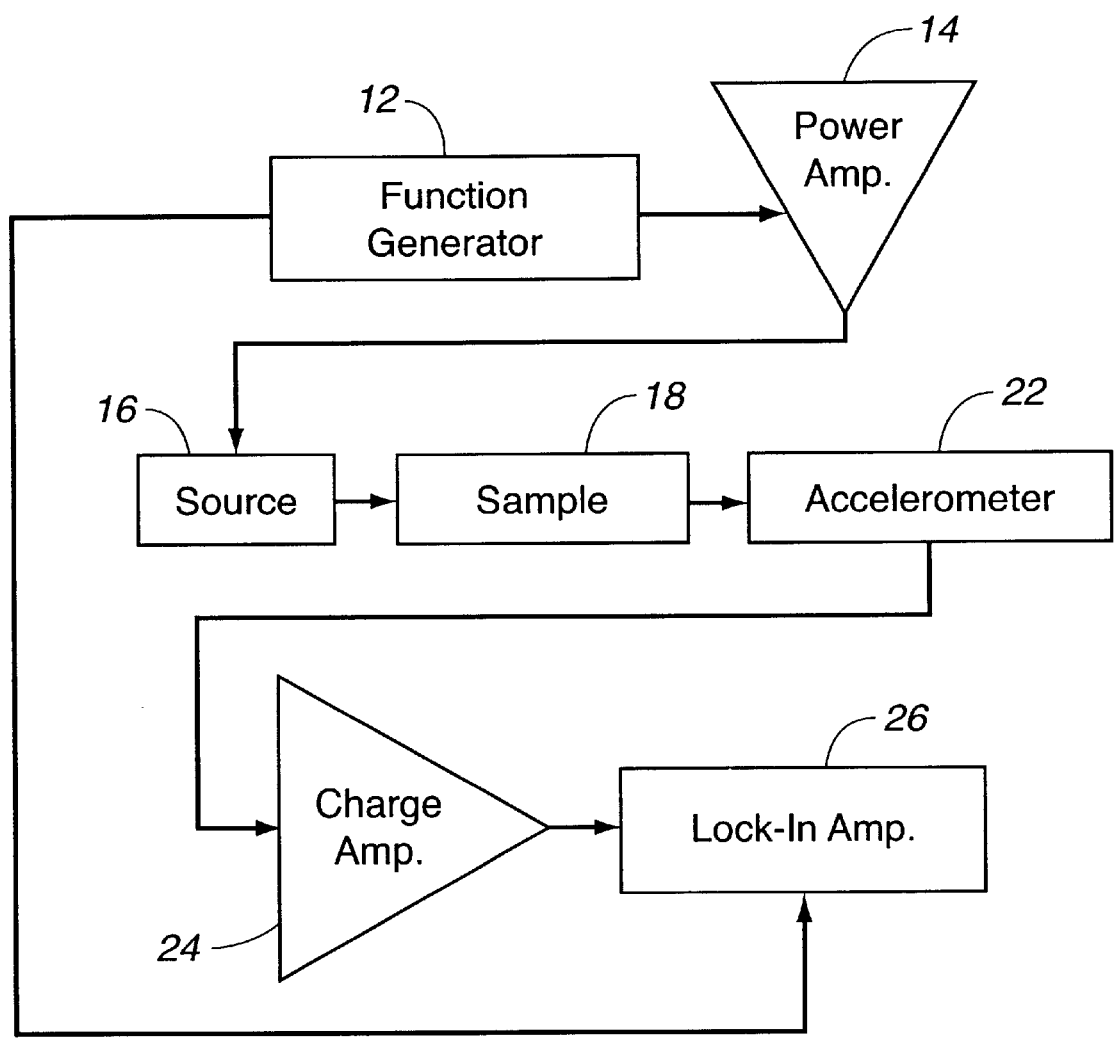
FIG. 1 is a block diagram schematic of data acquisition system according to the present invention.

The present invention relates to methods with which to characterize damage in materials by application of nonlinear elastic wave spectroscopy. The application of single mode nonlinear resonant ultrasound spectroscopy (SIMONRUS) to rocks and to numerous other materials has been well documented. These materials are called mesoscopic nonlinear materials because they have in common extreme nonlinearity, hysteresis, and/or discrete memory in their stress-strain behavior.

For example, two right-cylindrical cores of concrete, 4 cm in diameter, were examined: the first 8.8 cm long and the other 10.7 cm long. The samples were taken from different sections of highway pavement in the Albuquerque, N.M. area. The first sample was not visibly damaged; the second sample showed clear evidence of alkali-silica reactivity (ASR). ASR forms a gel around the particles of gravel used as aggregate, and in cracks in the paste matrix. The gel swells and shrinks with relative hydration, progressively distressing the concrete.

To minimize the effects of changes in humidity and temperature, the samples were isolated from the surroundings in a sealed, vibration-isolated, thermally-insulated box, in an atmosphere of dry $N_2$. The response characteristics of the samples were then obtained using the apparatus shown in block diagram form in FIG. 1. A sine wave signal, generated by a Hewlett-Packard 8904A waveform generator 12, was amplified 14 to drive a 4 cm diameter PZT-4 piezoelectric disk 16. The piezoelectric disk 16 has a high impedance (brass) backload, which was necessary to achieve adequate wave amplitudes in the sample 18. A Bruel & Kjaer 374 piezoelectric accelerometer 22 was bonded to the opposite end of the sample 18. The output signal from the accelerometer 22 was amplified by a Bruel & Kjaer 2635 charge amplifier 24, and the signal was then directed to an EG&G 5302 lock-in amplifier 26. Lock-in amplifier 26 also received a reference signal directly from waveform generator 12. The entire system was automated using LabVIEW software running on a PowerPC computer (not shown).

The above-described exemplary apparatus is presented for purposes of illustration and is not intended to limit the scope of the present invention. For example, the input acoustic wave could be applied though non-contact devices, such as audio speaker. The necessary function of the device is to apply a sweeping frequency input and detecting the resonant response of the workpiece at progressively increasing strain amplitudes.

To obtain experimental results, the input frequency was incrementally swept through an interval that contains the fundamental-mode resonance. At each drive frequency, the frequency, signal magnitude, and amplitude/phase of the detected signal were recorded. The strain amplitude, $\epsilon = \partial u / \partial x$, where u is the displacement, and x is the bar length, was calculated by taking a double integral in time of the measured acceleration amplitude, $\ddot{U}$, and dividing by the length of the workpiece, here a bar shape. The resonance frequency and the corresponding peak acceleration values were obtained using a nonlinear least-squares (Levenberg-Marquardt) fit to a Lorentzian curve at low amplitudes and to a polynomial fit at higher amplitudes (where the resonance curves become asymmetric). Additionally, the time, and the temperature, measured using a thermistor mounted inside the sample box, were recorded. In the tests reported below, the results were repeatable and, because they are conducted at very low strain amplitudes, no damage occured to the samples during experimentation.

A complete NRUS experiment provides three measures of nonlinear response. These include 1) the change in resonance frequency with strain amplitude, 2) the wave harmonic amplitudes, and 3) slow dynamics. The present invention relates to the measured change in resonance frequency with strain amplitude.

To determine the change in resonance frequency with strain amplitude, the frequency is swept through a range that envelops the first resonant mode, at a constant input voltage. In the example, the fundamental mode was chosen because of its greater signal strength; other modes would provide the same information. The input-signal voltage is then increased, and the procedure is repeated. The frequency sweeps may be varied in direction (increasing or decreasing frequency), frequency range, and duration.

Figure 2:
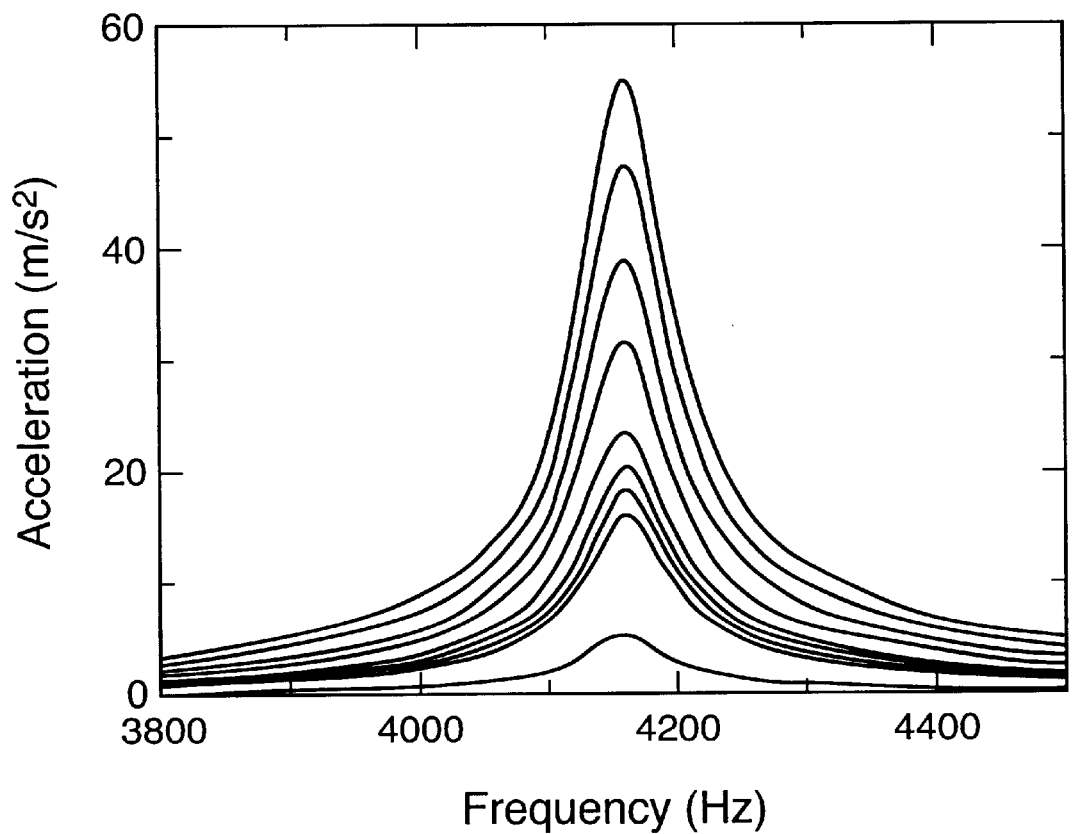
FIG. 2 graphically depicts the resonance response of an undamaged plexiglass sample.

In the strain ranges typically used for SIMONRUS, materials that are undamaged respond to elastic waves in a nearly linear manner. That is, the resonance frequency, which is proportional to modulus (calculated from the resonance frequency, the bar length, and the material density), is independent of the amplitude of the applied signal. As an example, the nearly linear response for Lucite is shown in FIG. 2.

Figure 3A:
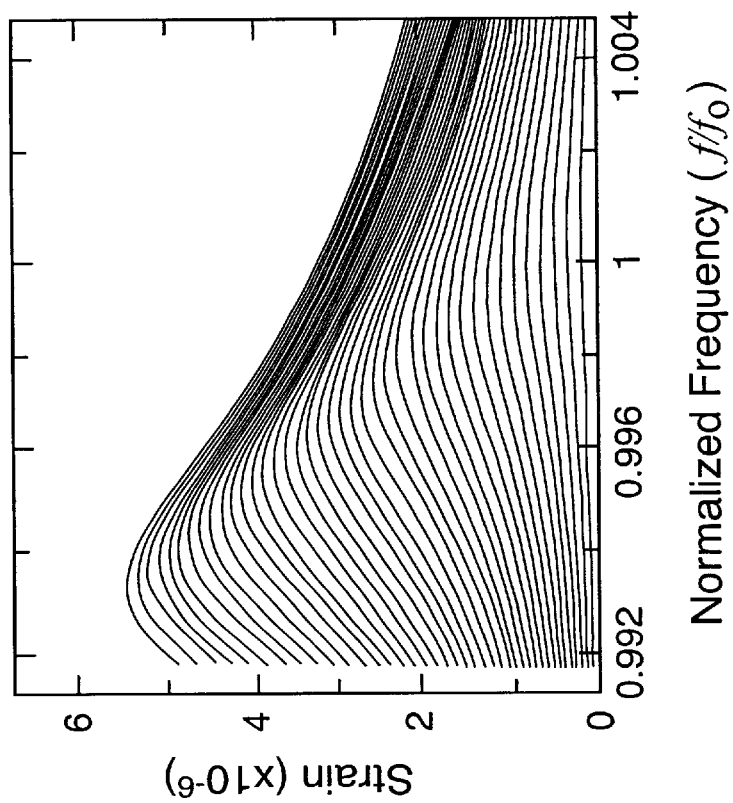
FIGS. 3A and 3B graphically depict the resonance response of undamaged and damaged concrete samples, respectively, to increasing applied strains.
Figure 3B:
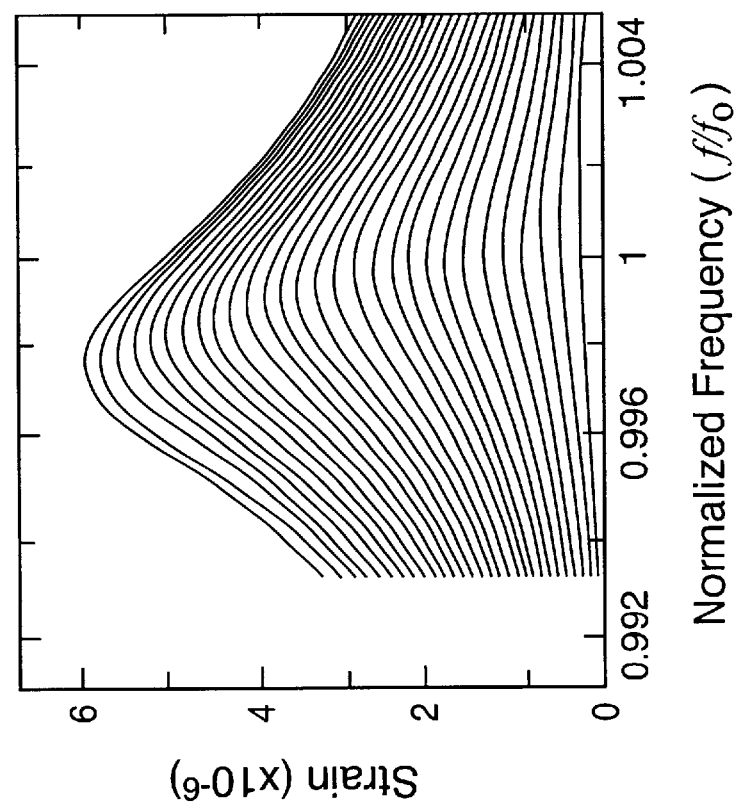

In contrast, it has been well demonstrated that complex disordered media, including rock and other damaged solids, such as metals with cracks or dislocations and the like, show a notable nonlinear response. FIGS. 3A and 3B show the nonlinear responses of the two concrete samples described above. Although the resonance-peak frequency decreases as the input-signal amplitude increases for both samples, the effect is significantly greater for the damaged sample. The expected, but smaller, nonlinearity in the undamaged sample (FIG. 3A) is the result of incipient compliant features, such as microcracks, which are found in any concrete. The nonlinearity in the damaged sample (FIG. 3B) is readily apparent from the resonance frequency shift with increasing strain.

In addition to the resonance shift, another aspect of the nonlinear signature of a material is a progressive asymmetry in the resonance curves as the strain increases. The resonance curves from the ASR-damaged concrete sample (FIG. 3B) become distinctly more asymmetric as the input-signal amplitude increases, and the distortion appears at much lower strain than in those of the undamaged sample. The conspicuously greater nonlinear behavior of the ASR-damaged sample is interpreted as due to the presence of additional ASR-associated microcracks.

In accordance with the present invention a quantitative measure of the nonlinear signature is identified by the scaling of the relative change in frequency ($|\Delta f/f_0|$) with the strain amplitude on logarithmic axes. Here, $f_0$ is the frequency of the resonance peak at the lowest amplitude of applied strain and $\Delta f$ is the frequency shift of the resonance peak at each of the applied strains. The Preisach-Mayegoyz model predicts a slope of 1 for hysteretic nonlinearity, and a slope of 2 for classical nonlinearity. A slope which is between 1 and 2 suggests a nonlinear mechanism.

Figure 4:
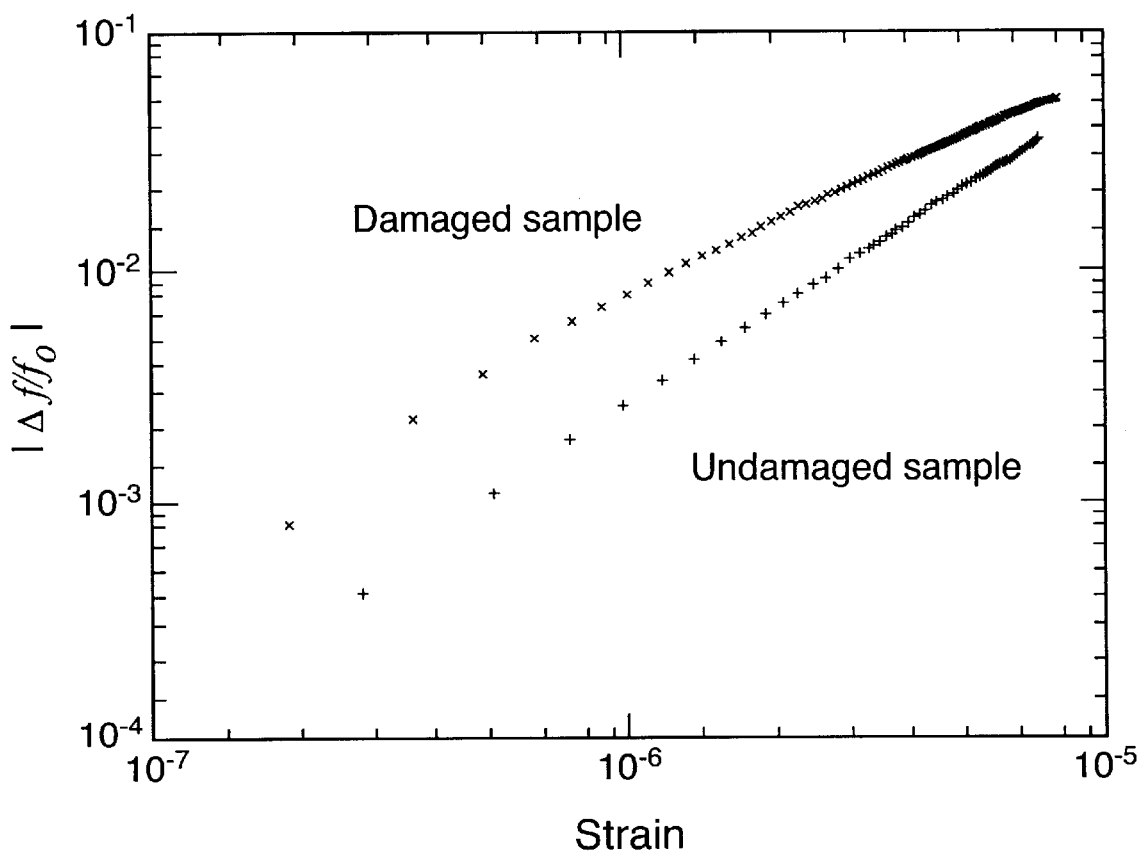
FIG. 4 graphically depicts the difference in normalized frequency shift of the samples tested for FIGS. 3A and 3B.

As graphically shown in FIG. 4, the slope for the ASR-damaged sample is approximately 1.3, whereas the slope of the undamaged sample is almost exactly 1. Throughout this strain range, the frequency shift of the ASR-damaged sample is always larger than that of the undamaged sample. Also, there is more frequency shift over equivalent strain intervals. That is, the slope is larger, meaning the material is more damaged and more nonlinear. In this way, the relative frequency shift with strain alone provides a sensitive discriminating diagnostic tool which clearly identifies the greater damage, in this case ASR-related microcracks.

Thus, nonlinear elastic resonance experiments provide several sensitive qualitative diagnostic measures of chemical and physical damage in concrete. It is apparent from the results herein that ASR-damaged concrete can be distinguished from undamaged concrete by its more nonlinear behavior. These results clearly show that the nonlinearity of a material, in this case directly related to chemical degradation, can be used to evaluate the condition of a material and to identify damage, even at extremely low strains. These techniques are sensitive to even small amounts of damage.

Other experiments have shown that an undamaged material, such as Pyrex® glass, has a response like that of the Lucite® shown in FIG. 2. When locally cracked, the Pyrex® glass showed a response like the concrete response shown in FIG. 3B. Thus, this method is useful for both volumetrically and locally damaged materials.

Figure 5A:
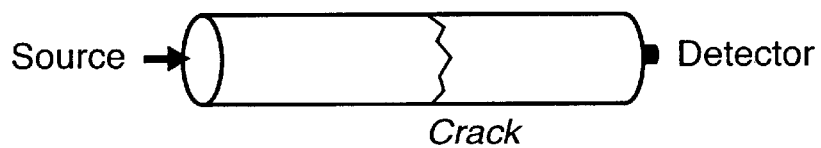
FIGS. 5A–C depict the application of the present invention to a Pyrex® rod.
Figure 5B:
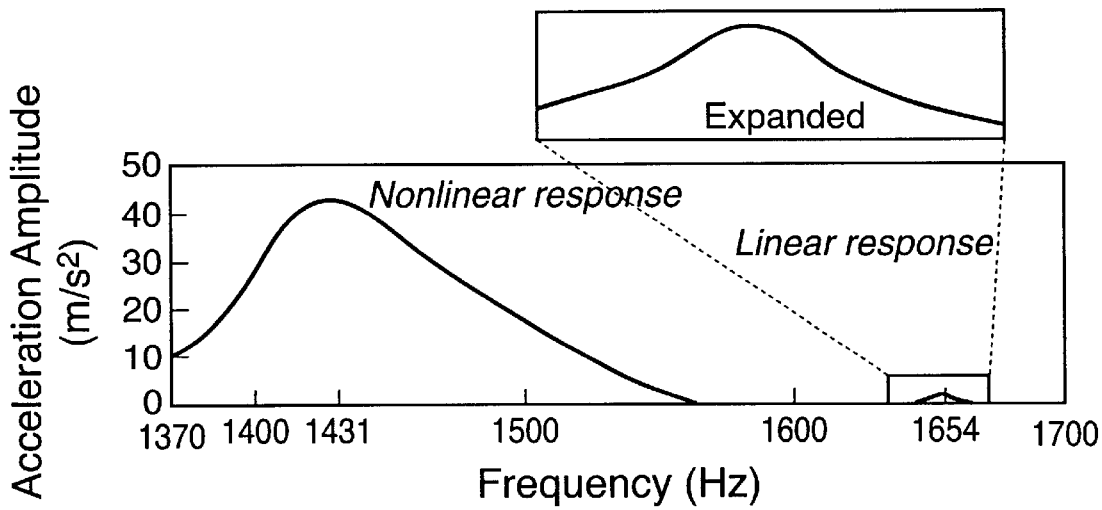
Figure 5C:
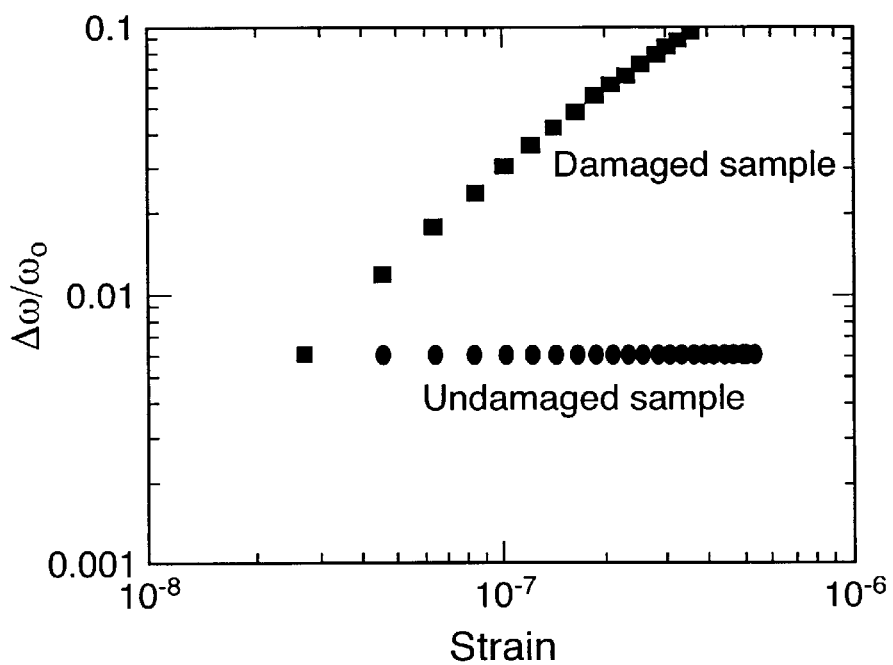

FIGS. 5A–5C show the experimental results from a Pyrex® glass rod. FIG. 5A illustrates the experimental configuration, where the rod is sample 18, as shown in FIG. 1. The response was first determined for undamaged material to obtain the linear response shown in FIG. 5B. The rod was then cracked near the rod center and the damage response was obtained as shown by the nonlinear response shown in FIG. 5B.

FIG. 5B depicts the acceleration amplitude response as a function of frequency at one strain level. FIG. 5C graphically depicts the ratio $\Delta\omega/\omega_0$ (the same as $(\Delta f/f_0)$) as a function of applied strain. The difference in the slopes for the damaged and undamaged response demonstrates the sensitivity of the present invention to detecting damage in components.

The foregoing description of the invention has been presented for purposes of illustration and description and is not intended to be exhaustive or to limit the invention to the precise form disclosed, and obviously many modifications and variations in, e.g., sample geometry and in the selected resonance mode, are possible in light of the above teaching.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for identifying components with defects using strains applied at acoustic and ultrasound frequencies, comprising the steps of:

a. determining the relative resonance frequency shift $|\Delta f/f_0|$ as a function of applied strain for an acceptable component, where $f_0$ is the frequency of the resonance peak at the lowest amplitude of applied strain and $\Delta f$ is the frequency shift of the resonance peak as strain amplitude is increased to determine a reference relationship;

b. determining the relative resonance frequency shift $|\Delta f/f_0|$ as a function of applied strain for a component under test, where $f_0$ is the frequency of the resonance peak at the lowest amplitude of applied strain and $\Delta f$ is the frequency shift of the resonance peak as strain amplitude is increased to determine a quality test relationship; and c. comparing the reference relationship with the quality test relationship to determine the presence of defects in the component under test.

2. A method according to claim 1, wherein the reference and quality test relationships are determined by a slope when $\log|\Delta f/f_0|$ is plotted against applied strain.

* * * * *